United States Patent [19]
Morikawa et al.

[11] Patent Number: 5,608,126
[45] Date of Patent: Mar. 4, 1997

[54] PROCESS FOR PREPARING 1,1,1,3,3-PENTAFLUOROPROPANE

[75] Inventors: Shinsuke Morikawa; Hidekazu Okamoto; Keiichi Ohnishi; Shin Tatematsu, all of Yokohama, Japan

[73] Assignee: AG Technology Co., Ltd., Yokohama, Japan

[21] Appl. No.: 494,063

[22] Filed: Jun. 23, 1995

[30] Foreign Application Priority Data

Jun. 28, 1994 [JP] Japan .................................. 6-146466

[51] Int. Cl.$^6$ ............................ C07C 17/08; C07C 21/18
[52] U.S. Cl. ............................ 570/167; 570/168; 570/172
[58] Field of Search .................................. 570/168, 172, 570/167

[56] References Cited

U.S. PATENT DOCUMENTS 5,300,710   4/1994   Corbin et al. ............................ 570/168

FOREIGN PATENT DOCUMENTS 0522639   1/1993   European Pat. Off. .
WO95/04021 2/1995   WIPO .

OTHER PUBLICATIONS

Journal of Flourine Chemistry, vol. 57, pp. 259–284, 1992, T. Tanuma, et al., "F Nuclear Magnetic Resonance Studies of Halogenated Propaines".

Database WPI, Derwent Publications, AN–92–281673 [34], JP–4–193841, Jul. 13, 1992.

*Primary Examiner*—Alan Siegel
*Attorney, Agent, or Firm*—Oblon, Spivak, McClelland, Maier & Neustadt, P.C.

[57] ABSTRACT

A process for preparing 1,1,1,3,3-pentafluoropropane, which comprises reacting 1,1-difluoroethylene with dichlorofluoromethane in the presence of a Lewis acid catalyst to form 1,2,2-trihydrodichlorotrifluoropropane and fluorinating the 1,2,2-trihydrodichlorotrifluoropropane with hydrogen fluoride.

15 Claims, No Drawings

PROCESS FOR PREPARING 1,1,1,3,3-PENTAFLUOROPROPANE

The present invention relates to a method for preparing 1,1,1,3,3-pentafluoropropane (hereinafter referred to as "R245fa"). R245fa is a hydrofluorocarbon (HFC) useful as a blowing agent which does not destroy the ozone layer.

As a process for preparing R245fa, there are known (1) a process for hydrogenating 1,1,3,3,3-pentafluoro-1-pentene in the presence of a palladium catalyst (Izvest. Akad. Nauk S.S.S.R., Otdel. Khim. Nauk. 1960, 1412) and (2) a process for hydrogen-reducing 1,1,3,3,3-pentafluoro-2,2,3-trichloropropane in the presence of a palladium catalyst (U.S. Pat. No. 2,942,036).

However, starting materials used in the above processes (1) and (2) are very expensive, and they are hard to be industrially available.

An object of the present invention is to provide a process for preparing R245fa, which does not have the above-mentioned disadvantages of the conventional processes. Thus, the present invention is to provide a process for easily preparing R245fa at high yield, which comprises reacting 1,1-difluoroethylene (hereinafter referred to as "2F") and dichlorofluoromethane (hereinafter referred to as "R21"), which are easily available at a low price in an industrial scale, in the presence of a Lewis acid catalyst to form 1,2,2-trihydrodichlorotrifluoropropane and fluorinating the 1,2,2-trihydrodichlorotrifluoropropane with hydrogen fluoride.

For explanation, the main reaction formula of the present invention is illustrated below. Starting materials used in the reaction of the present invention (2F and R21) are easily available in an industrial scale.

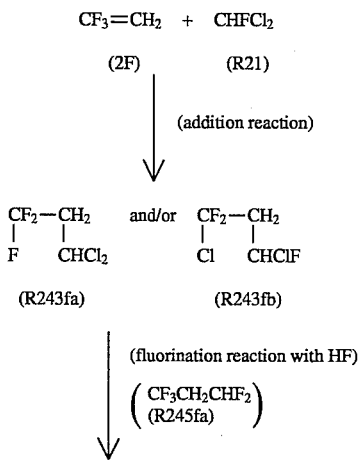

In the addition reaction for obtaining 1,2,2-trihydrodichlorotrifluoropropane (hereinafter simply referred to as "addition reaction"), 1,2,2-trihydrodichlorotrifluoropropane is obtained selectively when 2F and R21 are reacted in the presence of a Lewis acid catalyst. The term, "1,2,2-trihydrodichlorotrifluoropropane" means at least one member selected from the group consisting of 1,1-dichloro-3,3,3-trifluoropropane (R243fa) and 1,3-dichloro-1,1,3-trifluoropropane (R243fb). The product ratio of R243fa and R243fb varies depending on the type of a catalyst used, but both isomers can be converted to R245fa by fluorination reaction.

The molar ratio of 2F/R21 ranges from 0.5 to 1.5, preferably from 1.0 to 1.1. The addition reaction may be a batch-wise reaction or a continuous reaction wherein starting materials are continuously supplied to a reactor, from which the reaction product is continuously taken out, but a continuous reaction is preferable. The addition reaction of R21 and 2F is known from Japanese Unexamined Patent Publication No. 193841/1992.

Preferable examples of a Lewis acid catalyst used in the addition reaction include a halide or oxihalide of at least one element selected from the group consisting of B, Al, Ga and In of Group 13, Fe, Ni and Co of Iron Group, Ti, Zr and Hf of Group 4, Nb and Ta of Group 5, and Sb, Sn and W, and elements of Group 13, Group 4 and Group 5 are particularly preferable.

Examples of the halide catalyst include halides of B, Al, Ga, In, Fe, Ni, Co, Sb, Nb, Sn, Ti, Zr, Hf and W, and for example, a chloride, a fluoride or a chlorofluoride is preferable.

More particular preferable examples include $BF_3$, $AlCl_3$, $AlCl_2F$, $AlClF_2$, $GaCl_3$, $InCl_3$, $FeCl_2$, $FeCl_3$, $NiCl_2$, $CoCl_2$, $SbCl_5$, $SbF_5$, $SbCl2F_3$, $NbCl_5$, $SnCl_4$, $TiCl_4$, $TiCl2F_2$, $ZrCl_4$, $ZrCl_3F$, $ZrCl_2F_2$, $ZrClF_3$, $HfCl_4$, $HfClF_3$, $WCl_6$, $TaCl_5$ and the like.

Examples of the oxihalide catalyst include compounds prepared by treating an oxide of the above-mentioned one element or a mixed oxide of the above-mentioned at least two elements with an appropriate halogenating agent such as a chlorofluorocarbon including trichlorofluoromethane (hereinafter referred to as "R11"), dichlorodifluoromethane (hereinafter referred to as "R12"), 1,1,2-trichloro-1,2,2-trifluoroethane or the like, a hydrochlorofluorocarbon including R21, chlorodifluoromethane or the like, or chlorine, hydrogen fluoride, fluorine, and the like.

The halide or oxihalide catalyst of the above-mentioned elements may optionally contain at least one element such as Si, Zn, Mg, Cr, Cu, V, Bi, Mo and the like, other than the above-mentioned elements. In this case, these Si, Zn, Mg, Cr, Cu, V, Bi and Mo elements are generally contained in the form of a halide or an oxihalide.

The preparing conditions of the oxihalide catalyst vary depending on an oxide and a halogenating agent used, but usually the halogenating agent is used in an excess amount to the oxide.

A temperature employed in the preparation of the oxihalide catalyst is usually from 100° to 500° C., preferably from 200° to 450° C., when the catalyst preparation is conducted in the gas phase, and is usually from 0° to 200° C., preferably from 20° to 120° C., when the catalyst preparation is conducted in the liquid phase.

The amount of a Lewis acid catalyst present in the addition reaction is usually from 0.01 to 50 parts by weight, preferably from 0.1 to 10 parts by weight, per 100 parts by weight of the total starting materials (2F and R21) in a reactor of batch-wise reaction or per 100 parts by weight of the total starting materials (2F and R21) staying in a reactor of continuous reaction.

The reaction temperature of the addition reaction is usually from −40° C. to +200° C., preferably from −10° C. to +100° C. The reaction pressure of the addition reaction is not specially limited, and may be atmospheric pressure, but it is usually preferable to employ from a pressure slightly higher than atmospheric pressure to 10 kg/cm² (gauge pressure).

The addition reaction may be either a gas phase reaction or a liquid phase reaction, but it is preferable to employ a liquid phase reaction, in which an amount of a side reaction product is smaller. The reaction may be conducted in an inert solvent such as perfluorooctane and perfluoro(2-butyltetrahydrofuran). In order to make purification easy, it is usually preferable not to use a solvent other than starting materials and reaction products.

The fluorination reaction for obtaining the desired R245fa by fluorinating 1,2,2-trihydrodichlorotrifluoropropane with hydrogen fluoride (hereinafter simply referred to as "fluorination reaction") may be either a liquid phase reaction or a gas phase reaction. However, it is usually preferable to employ a liquid phase reaction since an amount of a side reaction product is smaller. The fluorination reaction may be either a batch-wise reaction or a continuous reaction wherein starting materials are continuously supplied to a reactor and a reaction product is continuously withdrawn from the reactor. However, a continuous reaction is preferable.

A reaction product containing R243fa and R243fb obtained by the addition reaction may be used as it is as a starting material (1,2,2-trihydrodichlorotrifluoropropane) to be subjected to fluorination reaction, or a mixture of R243fa and R243fb only separated from the reaction product may be subjected to fluorination reaction. Also, R243fa and R243fb separated from the reaction product may be separately subjected to fluorination reaction.

Since the reactivity of R243fa with hydrogen fluoride is higher than that of R243fb, it is preferable to make the mixing ratio of R243fa higher when preparing a mixture of R243fa and R243fb to the be supplied to fluorination reaction. Also, R243fa only separated from a mixture of R243fa and R243fb may be supplied to fluorination reaction.

As a fluorination catalyst used in a liquid phase fluorination with hydrogen fluoride, it is preferable to employ a halide of at least one element selected from the group consisting of Sb, Nb, Ta and Sn, for example, chloride, fluoride or chlorofluoride. Particularly preferable examples include $SbF_5$, $SbCl_5$, $SbCl_2F_3$, $NbCl_5$, $NbClF_4$, $NbF_5$, $TaF_5$, $TaCl_5$, $TaClF_4$, $SnCl_4$, $SnClF_3$ and the like.

The above fluorination catalyst is generally present in an amount of from 0.01 to 50 parts by weight, preferably from 0.1 to 10 parts by weight, per 100 parts by weight of 1,2,2-trihydrodichlorotrifluoropropane in the reactor of batch-wise reaction or per 100 parts by weight of 1,2,2-trihydrodichlorotrifluoropropane staying in the reactor of continuous reaction. However, it should be noted that the amount of the fluorination catalyst is not limited to the above-mentioned values.

The liquid phase fluorination reaction is preferably conducted under a pressure of atmospheric pressure or pressurized condition at a temperature in the range of from 0° C. to 200° C., particularly from 20° C. to 150° C. The reaction may be conducted by using a solvent other than raw materials and reaction product. In this case, the solvent used is not specially limited as long as it dissolves raw materials and it is hardly fluorinated than the raw materials. Examples of the solvent include hydrofluorocarbons other than R245fa, perfluorocarbons such as perfluorooctane, or perfluoropolyethers.

An amount of hydrogen fluoride to be supplied to 1,2,2-trihydrodichlorotrifluoropropane is not specially limited as long as it is at least 2 mols (stoichiometric amount=2) to one mol of 1,2,2-trihydrodichlorotrifluoropropane. However, it is preferable to employ hydrogen fluoride in an amount of from 2 to 20 mols, particularly from 2 to 10 mols, when taking reactor efficiency and recovery of hydrogen fluoride into consideration. Hydrogen fluoride may be previously charged before reaction, or may be charged into a liquid phase during reaction. It is usually preferable to charge hydrogen fluoride into a liquid phase during reaction.

The reaction pressure is usually from 0 to 20 kg/cm² (gauge pressure), but it may vary depending on the type of a solvent used when a solvent other than raw materials and reaction products is used.

EXAMPLES

PREPARATION EXAMPLE 1

1000 g of commercially available γ-alumina was dried to remove moisture, and was then chlorofluorinated at a temperature of from 100° to 300° C. in a mixed gas stream of R12/nitrogen to obtain an oxihalide catalyst.

PREPARATION EXAMPLE 2

1000 g of zirconium oxide was obtained by calcinating a precipitate that was made from zirconium nitrate aqueous solution and aqueous ammonia. Then, it was dried to remove moisture, and was chlorofluorinated at a temperature of from 150° to 400° C. in a mixed gas stream of R12/nitrogen to obtain an oxihalide catalyst.

PREPARATION EXAMPLE 3

1000 g of titanium oxide was obtained by calcinating a precipitate that was made from titanium tetrachloride aqueous solution and aqueous ammonia. Then, it was dried to remove moisture, and was then chlorofluorinated at a temperature of from 100° to 400° C. in a mixed gas stream of R11/nitrogen to obtain an oxihalide catalyst.

EXAMPLE 1

20 g of $AlCl_3$ was placed in a 2l-Hastelloy C autoclave, and 1200 g (11.65 mol) of R21 was added in the reactor after degassing under reduced pressure. The 2F was continuously added thereto while maintaining the autoclave at −20° C. After adding 760 g (11.88 mol) of 2F, the reaction mixture was stirred for further 1 hour, and the reaction mixture was filtrated to recover 1920 g of crude products. The composition of the reaction crude products thus recovered was analyzed by gas chromatography and $^{19}F$-NMR, and the results are shown in the following Table 1 (unit: mol %, the same as in the other Examples).

The crude products were distilled to obtain 1680 g of a mixture of R243fa and R243fb. Thereafter, 1680 g (10.06 mol) of the mixture of R243fa and R243fb, 20 g of $SbCl_5$ and 600 g of hydrogen fluoride (30 mol) were charged into a reactor of a 5l-Hastelloy C autoclave equipped with a condenser cooled at 0° C., and the reaction was conducted at a temperature of 80° C. after degassing.

While purging by-product HCl through the condenser at 0° C., the reaction was conducted for 10 hours by maintaining the reaction pressure at 10 kg/cm² (gauge pressure). Then, the whole amount (1310 g) of the crude products were recovered after passing through an alkali-neutralization tank. The composition of the recovered crude products was analyzed by gas chromatography and 19F-NMR, and the analysis results are shown in the following Table 2 (unit: mol %, the same as in the other Examples).

EXAMPLE 2

R21 was reacted with 2F in the same manner as in Example 1, except that 20 g of $ZrCl_4$ was used in place of 20 g of $AlCl_3$, and the reaction mixture was filtrated to recover 1912 g of the crude products. The composition of the crude products thus recovered was analyzed in the same manner as in Example 1, and the results are shown in the following Table 1.

This crude products were distilled to obtain 1750 g of a mixture of R243fa and R243fb. Fluorination reaction was conducted in the same manner as in Example 1, except for using 1750 g of the above obtained mixture of R243fa and R243fb, thereby producing 1320 g of crude products. The composition of the crude products was analyzed in the same manner as in Example 1, and the results are shown in the following Table 2.

EXAMPLES 3 to 5

R21 was reacted with 2F in the same manner as in Example 1, except for using 20 g of a catalyst prepared by each of the above Preparation Examples 1 to 3. The reaction mixture was filtrated to obtain crude products, the composition of which was analyzed in the same manner as in Example 1, and the results are shown in the following Table 1. The crude products thus obtained were used as they were without distilling, and were subjected to fluorination reaction in the presence of 20 g of a catalyst respectively shown in the following Table 2 in the same manner as in Example 1. The composition of the crude products thus obtained was analyzed in the same manner as in Example 1, and the results are shown in the following Table 2.

TABLE 1

| Example<br>Catalyst | 1<br>AlCl$_3$ | 2<br>ZrCl$_4$ | 3<br>Preparation<br>Example 1 | 4<br>Preparation<br>Example 2 | 5<br>Preparation<br>Example 3 |
|---|---|---|---|---|---|
| R21 | 0 | 0.1 | 0.1 | 0.8 | 2.0 |
| 2F | 0.1 | 0.2 | 0.2 | 0.2 | 0.5 |
| R243fa | 91 | 83 | 88 | 77 | 72 |
| R243fb | 3 | 13 | 10 | 21 | 25 |
| Others | 5.9 | 3.7 | 1.7 | 1.0 | 0.5 |

TABLE 2

| Example<br>Catalyst | 1<br>SbCl$_5$ | 2<br>SbCl$_5$ | 3<br>SbCl$_5$ | 4<br>TaCl$_5$ | 5<br>NbCl$_5$ |
|---|---|---|---|---|---|
| R245fa | 97 | 98 | 94 | 97 | 88 |
| CF$_3$CH=CHCl | 0.3 | 0.4 | 0.2 | 0.1 | 0.5 |
| CF$_3$CH$_2$CHClF | 0.8 | 0.6 | 0.8 | 0.2 | 1.8 |
| R243fa | 1.2 | 0.5 | 1.0 | 0.3 | 4.0 |
| R243fb | 0 | 0.1 | 0.2 | 0.1 | 2.5 |
| Others | 0.7 | 0.4 | 3.8 | 2.3 | 3.2 |

As illustrated in the above Examples, the present invention has an effect of easily producing R245fa in a high yield in an industrial scale, which has been hardly produced in an industrial scale heretofore.

What is claimed is:

1. A process for preparing 1,1,1,3,3-pentafluoropropane, which comprises reacting 1,1-difluoroethylene with dichlorofluoromethane in the presence of a Lewis acid catalyst to form 1,2,2-trihydrodichlorotrifluoropropane, and fluorinating the 1,2,2-trihydrodichlorotrifluoropropane with hydrogen fluoride at a temperature of from 0° C. to 200° C.

2. The process according to claim 1, wherein the Lewis acid catalyst is a halide or oxihalide of at least one element selected from the group consisting of B, Al, Ga, In, Fe, Ni, Co, Sb, Nb, Sn, Ti, Zr, Hf, W and Ta.

3. The process according to claim 1, wherein the Lewis acid catalyst is present in an amount of from 0.01 to 50 parts by weight per 100 parts by weight of the total of 1,1-difluoroethylene and dichlorofluoromethane.

4. The process according to claim 1, wherein 1,1-difluoroethylene is reacted with dichlorofluoromethane in a molar ratio of 0.5–1.5 to 1.

5. The process according to claim 1, wherein the reaction of 1,1-difluoroethylene with dichlorofluoromethane is conducted at the temperature in the range from −40° C. to +200° C.

6. The process according to claim 1, wherein the reaction of 1,1-difluoroethylene with dichlorofluoromethane is conducted in liquid phase.

7. The process according to claim 1, wherein the fluorination is conducted in the presence of a fluorination catalyst comprising a halide of at least one element selected from the group consisting of Sb, Nb, Ta and Sn.

8. The process according to claim 1, wherein hydrogen fluoride is supplied in a molar ratio of from 2 to 20 mols to 1 mol of 1,2,2-trihydrodichlorotrifluoropropane.

9. The process according to claim 1, wherein the fluorination reaction is a liquid phase reaction.

10. The process according to claim 1, wherein the 1,2,2-trihydrodichlorotrifluoropropane is at least one member selected from the group consisting of 1,1-dichloro-3,3,3-trifluoropropane and 1,3-dichloro-1,1,3-trifluoropropane.

11. A process for preparing 1,1,1,3,3-pentafluoropropane, which comprises fluorinating 1,2,2-trihydrodichlorotrifluoropropane with hydrogen fluoride at a temperature of from 0° C. to 200° C.

12. The process according to claim 11, wherein the fluorination is carried out in the presence of a fluorination catalyst comprising a halide of at least one element selected from the group consisting of Sb, Nb, Ta and Sn.

13. The process according to claim 11, wherein hydrogen fluoride is supplied in a molar ratio of from 2 to 20 mols to 1 mol of 1,2,2-trihydrodichlorotrifluoropropane.

14. The process according to claim 11, wherein the fluorination reaction is conducted in a liquid phase.

15. The process according to claim wherein the 1,2,2-trihydrodichlorotrifluoropropane is selected at least from the group consisting of 1,1-dichloro-3,3,3-trifluoropropane and 1,3-dichloro-1,1,3-trifluoropropane.

* * * * *